United States Patent [19]

Cabrera

[11] Patent Number: 5,213,800
[45] Date of Patent: May 25, 1993

[54] CHLORHEXIDINE DISINFECTANT GRANULES

[75] Inventor: Francisco Cabrera, Des Moines, Iowa

[73] Assignee: Diamond Scientific Company, Des Moines, Iowa

[21] Appl. No.: 470,295

[22] Filed: Jan. 25, 1990

Related U.S. Application Data

[63] Continuation of Ser. No. 309,270, Feb. 9, 1989, abandoned.

[51] Int. Cl.⁵ ............... A01N 25/28; A01N 33/06; A01N 33/06
[52] U.S. Cl. ................... 424/417; 424/405; 424/408; 514/635
[58] Field of Search ......... 514/187; 424/404, 405, 424/406, 408, 409, 717, 83

[56] References Cited

U.S. PATENT DOCUMENTS

| | | | |
|---|---|---|---|
| 3,553,139 | 1/1971 | McCarty | 252/95 |
| 3,818,076 | 6/1974 | Edwards | 260/501.11 |
| 4,177,254 | 12/1979 | Khan et al. | 424/16 |
| 4,269,821 | 5/1981 | Kreuter et al. | 424/19 |
| 4,501,726 | 2/1985 | Schroder et al. | 424/1.1 |
| 4,602,011 | 7/1986 | West et al. | 514/187 |
| 4,732,765 | 3/1988 | Sasagawa et al. | 424/476 |
| 4,744,989 | 5/1988 | Payne et al. | 424/490 |
| 4,816,265 | 3/1989 | Cherukuri et al. | 426/5 |
| 4,856,541 | 8/1989 | Kellet et al. | 132/110 |
| 4,871,549 | 10/1989 | Ueda et al. | 424/484 |
| 4,933,190 | 6/1990 | Cherukuri et al. | 426/5 |
| 4,981,698 | 1/1991 | Cherukuri | 426/5 |

FOREIGN PATENT DOCUMENTS

| | | | |
|---|---|---|---|
| 8213073 | 12/1983 | European Pat. Off. | 424/490 |
| 0156243 | 10/1985 | European Pat. Off. | 424/493 |
| 8603675 | 7/1986 | PCT Int'l Appl. | 424/490 |

*Primary Examiner*—Thurman K. Page
*Assistant Examiner*—Neil Levy
*Attorney, Agent, or Firm*—Joseph C. Gil; Lyndanne M. Whalen

[57] ABSTRACT

Flowable, highly water soluble discrete particle disinfecting composition of chlorhexidine are provided. The composition is powdery in nature and makes chlorhexidine suitable for a general use, all purpose disinfectant for veterinary uses. It is comprised of a substrate of polyhydric alcohol coated with an encapsulating effective amount of a compatible surfactant, followed by a thin disinfecting coating of chlorhexidine.

9 Claims, No Drawings

CHLORHEXIDINE DISINFECTANT GRANULES

This application is a continuation of application Ser. No. 07/309,270, filed Feb. 9, 1989, now abandoned.

BACKGROUND OF THE INVENTION

This invention relates to disinfecting composition which contain the disinfectant compound chlorhexidine [1,6-di(4'chlorophenyl-diguanido)hexane]. The compositions possess advantageous properties from the standpoint of water dispersibility and flowability such that they can be conveniently packaged and used as an all purpose veterinary disinfectant.

Chlorhexidine acetate is a known disinfectant. It is, however, not easily water soluble. This limitation has made it difficult to use as an all purpose disinfectant, for example for use by veterinarians in a convenient concentrated form. There is a continuing need for an all purpose general use disinfectant in veterinary offices, one which can be used to clean for example tables, cages, floors, and even for use in surgical instruments.

Because of the solubility problems with chlorhexidine acetate, in spite of its known excellent disinfecting properties, it has not been sold in a convenient solid phase form. In particular, it is most commonly sold as a solution concentrate. However, the form of the solution concentrate for a disinfectant would seem substantially less preferred by veterinarians than a dry powder form since it requires a larger storage space.

Accordingly, it can be seen that there is a continuing need for the development of a water dispersible dry form chlorhexidine disinfecting composition. This invention has as its primary objective the fulfilling of this need. Another objective of the present invention is to provide a discrete particle, flowable disinfecting composition containing chlorhexidine in a stable dry form.

A yet further objective of the present invention is to provide a process of preparing a dry flowable, highly water soluble chlorhexidine disinfecting composition.

An even further objective of the present invention is to provide packaged and stable chlorhexidine disinfecting compositions.

The method and manner of accomplishing each of the above objectives will become apparent from the detailed description of the invention which follows.

SUMMARY OF THE INVENTION

This invention relates to chlorhexidine disinfecting compositions. In particular, a water soluble, flowable polyhydric alcohol substrate is coated with an encapsulating effective amount of a compatible surfactant. The surfactant is preferably a nonionic surfactant, but may also be a cationic surfactant. This coated particle is then covered by a substantially continuous layer of disinfecting chlorhexidine acetate powder.

This invention employs as a carrier for the chlorhexidine known solid pharmaceutical carriers such as starches, talc, sorbitol, mannitol, xylitol, and the like. These are powder materials. The preferred powder materials are polyhydric alcohols, and the most preferred as sorbitol, mannitol, and xylitol. Generally speaking, however, and in the broadest sense any polyhydric alcohol may be used as long as it is flowable, water soluble, compatible with chlorhexidine and capable of functioning as an effective substrate for supporting chlorhexidine. Preferred are $C_6$ to $C_{10}$ polyhydric alcohols, and most preferred are $C_6$ polyhydric alcohol such as sorbitol, mannitol, and xylitol.

The amount of polyhydric alcohol can generally vary within the weight percentage range of from about 48% to about 68%, preferably from about 53% to about 63%.

The disinfecting composition, of course, contains as its active disinfectant chlorhexidine. Chlorhexidine is present in an amount by weight of from about 10% to about 30%, preferably from about 15% to about 25%.

The composition also contains an encapsulating effective amount of a surfactant which is compatible both with the polyhydric alcohol substrate and with the chlorhexidine. Suitable surfactants are selected from nonionic and cationic surfactants. The most preferred are nonionic surfactants. Fatty alcohol ethoxylates have been known to perform very satisfactorily. The amount of the surfactant can vary within the range of from about 10% by weight to about 30% by weight, preferably from about 15% by weight to about 25% by weight.

In terms of the disinfecting composition, the three ingredients, namely the substrate polyhydric alcohol, the surfactant and the chlorhexidine disinfectant are the major ingredients.

Other minor ingredients may, of course, be added such as antioxidants, preservative agents, perfumes, small amounts of silicon dioxide for flowability, and the like. Generally, by way of summary, the composition can be within the range listed in Table I below.

TABLE I

| Components | Broad Range | Preferred | Best |
|---|---|---|---|
| Chlorhexidine | 10–30 | 15–25 | 19.0 |
| Polyhydric alcohol | 48–68 | 53–63 | 56.85 |
| Triton X100 | 10–30 | 15–25 | 20.0 |
| Silicon Dioxide | 0.5–3 | 1–2.5 | 1.6 |
| Sodium Nitrite | 0.5–1.7 | 0.9–1.3 | 1.0 |
| Perfume | 0.08–0.2 | 0.1–0.18 | 0.14 |
| FD&C Blue #1 (dye) | 0.01–0.05 | 0.02–0.03 | 0.024 |
| FD&C Yellow #5 (dye) | 0.01–0.04 | 0.016–0.02 | 0.018 |

The surfactants which may be used for this surfactant portion of the chlorhexidine disinfecting compositions of this invention, as heretofore mentioned, are preferably nonionic surfactants. Those include the following. The nonionics can be broadly defined as compounds produced by the condensation of alkylene oxide groups (hydrophilic in nature) with an organic hydrophobic compound, which may be aliphatic or alkyl aromatic in nature. The length of the hydrophilic or polyoxyalkylene radical which is condensed with any particular hydrophobic group can be readily adjusted to yield a water-soluble compound having the desired degree of balance between hydrophilic and hydrophobic elements. Another class has semi-polar characteristics.

(1) A class of nonionic synthetic surfactants under the trade name of PLURONIC. These compounds are formed by condensing ethylene oxide with a hydrophobic base formed by the condensation of propylene oxide with propylene glycol. The hydrophobic portion of the molecule which of course, exhibits water insolubility, has a molecular weight of from about 1500 to about 1800. The addition of polyoxyethylene radicals to this hydrophobic portion tends to increase the water solubility of the molecule as a whole and the liquid character of the product is retained up to the point where the polyoxyethylene content is about 50% of the total weight of the condensation product.

(2) The polyethylene oxide condensates of alkyl phenols, e.g., the condensation products of alkyl phenols having an alkyl group containing from about 6 to 12 carbon atoms in either a straight chain or branched chain configuration with ethylene oxide, the said ethylene oxide being present in amounts equal to 5 to 25 moles of ethylene oxide per mole of alkyl phenol. The alkyl substituent in such compounds may be derived from polymerized propylene, disobutylene, octene, or nonene, for example.

(3) Those nonionic surfactants derived from the condensation of ethylene oxide with the product resulting from the reaction of propylene oxide and ethylene diamine. For example, compounds containing from about 40% to about 80% polyoxyethylene by weight and having a molecular weight of from about 5,000 to about 11,000 resulting from the reaction of ethylene oxide groups with a hydrophobic base constituted of the reaction product of ethylene diamine and excess propylene oxide, said base having a molecular weight of the order of 2,500 to 3,000 are satisfactory.

(4) The condensation product of aliphatic alcohols having from 8 to 22 carbon atoms, in either straight chain or branched chain configuration, with ethylene oxide, e.g., a coconut alcohol-ethylene oxide condensate having from 5 to 30 moles of ethylene oxide per mole of coconut alcohol, the coconut alcohol fraction having from 10 to 14 carbon atoms.

(5) The anmonia, monoethanol and diethanol amides of fatty acids having an acyl moiety of from about 8 to about 18 carbon atoms. These acyl moieties are normally derived from naturally occurring glycerides, e.g. coconut oil, palm oil, soybean oil and tallow, but can be derived synthetically, e.g., by the oxidation of petroleum, or by hydrogenation of carbon monoxide by the Fischer-Tropsch process.

In addition to the three component major ingredients, the composition also contains minors. Minors refer to those ingredients which are present in smaller amounts, such as silicon dioxide for flowability, antioxidants for stability, dyes and preservatives.

Suitable antioxidants may be ascorbic acid, isoascorbic acid, salts of sulfurous acid, sodium formaldehydesulfoxylate, sodium nitrite, BHA, BHT, gallates and tocopherols.

The chlorhexidine is preferably pulverized to pass through a 80-200 mesh screen, standard size. The composition is prepared in the following manner. The color dyes are mixed in water to dissolve them. The colored solution is transferred to the mixing vessel, and sodium nitrite is added to mix. The surfactant is then added, along with perfume, and it is mixed for about 3-5 minutes.

The polyhydric alcohol is then rapidly stirred in while continuously mixing and stirring is continued until it is homogeneous, generally for from about 5 to about 10 minutes. Thereafter, the chlorhexidine is slowly added while mixing continuous for up to about 5 more minutes. If desired, silicon dioxide is then added until it is free flowing, generally mixing will continue for 5 to 10 more minutes. Finally, the composition is run through a screen (8-12 mesh) to break up any agglomerates.

The moisture content of the composition should generally be within the following range, 0.5% to 5%. The procedure may be summarized by the following:

Procedure

1. Measure water in a suitable container.
2. Add colors and mix to dissolve.
3. Transfer the colored solution to a mixing vessel (Nauta mixer, Pony Day Mixer, Ross Mixer, Ribbon blender, or other mixer suitable for wet granulations).
4. Add sodium nitrite and mix.
5. Add surfactant and perfume. Mix 3-5 minutes.
6. Add sorbitol rapidly while mixing. Continue mixing until homogeneous (5-10 minutes).
7. Add chlorhexidine slowly while mixing. Mix 5 minutes.
8. Add silicon dioxide until free flowing (5-10 minutes).
9. Run through a screen (8-12 mesh) if needed to break agglomerates.

The procedure may also be carried out in the following manner:

Procedure

1. Follow steps 1-5 above.
2. Add chlorhexidine and mix 5-10 minutes to obtain a homogeneous suspension.
3. Add the sorbitol rapidly while mixing. Continue to mix 5-10 minutes until homogeneous.
4. Add silicon dioxide and mix until free flowing.
5. Run through an 8-12 mesh screen if needed to break agglomerates.

The following example is offered to further illustrate but not limit the process of the present invention.

EXAMPLE

First, 0.03 g FD&C Blue #1, 0.04 g FD&C Yellow #5, and 0.75 p water is mixed. 1.7 g sodium nitrate is then added and mixed. 35 g triton X100 next added and mixed, followed by 31.65 g chlorhexidine diacetate. All is mixed until homogeneous. Next 0.24 g perfume added to the mixture, and then 95.7 g sorbitol. A thorough mixing is done after each addition. Finally, 2.7 g silicon dioxide is added and mixed until a free flowing powder is obtained. This is then run through an 8-12 screen to break agglomerates. The composition is then packaged in a 3 g plastic or foil packets, or in multiple use jars with a 3 g dispenser measure enclosed (3 g will make one gallon of disinfectant solution in water).

The packaged product is tested and found to be water dispersible, flows easily, is stable for up to two months when packaged, and functions as an effective disinfectant by simply dissolving 3 g in a gallon of water to provide an all purpose disinfectant, primarily for veterinary uses.

What is claimed is:

1. A dry flowable, water dispersible, discrete particle disinfecting composition comprising:
   a water soluble, flowable, solid polyhydric alcohol substrate encapsulated in a compatible surfactant; and coated with chlorhexidine.

2. The composition of claim 1 wherein the surfactant is a nonionic surfactant.

3. The composition of claim 2 wherein said surfactant is a fatty alcohol ethoxylate.

4. The composition of claim 1 wherein the polyhydric alcohol is sorbitol.

5. The composition of claim 1 wherein the chlorhexidine is in the form of chlorhexidine diacetate.

6. The composition of claim 1 wherein the polyhydric alcohol is within the range of from about 48% by weight to about 68% by weight of said composition.

7. A dry, flowable, water dispersible, discrete particle disinfecting composition comprising:

a water soluble, flowable, solid polyhydric alcohol substrate encapsulated in a compatible surfactant; and coated with from about 10% by weight to about 30% by weight of chlorhexidine.

8. The composition of claim 7 wherein the amount of chlorohexidine is from about 15% by weight to about 25% by weight.

9. The composition of claim 6 wherein the polyhydric alcohol is within the range of from about 53% by weight to about 63% by weight of said composition.

* * * * *